US010232181B2

(12) United States Patent
Rao et al.

(10) Patent No.: US 10,232,181 B2
(45) Date of Patent: Mar. 19, 2019

(54) TECHNIQUES FOR CURRENT STEERING DIRECTIONAL PROGRAMMING IN A NEUROSTIMULATION SYSTEM

(71) Applicant: BOSTON SCIENTIFIC NEUROMODULATION CORPORATION, Valencia, CA (US)

(72) Inventors: Prakash Rao, Philadelphia, PA (US); Sridhar Kothandaraman, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 281 days.

(21) Appl. No.: 14/200,702

(22) Filed: Mar. 7, 2014

(65) Prior Publication Data

US 2014/0277262 A1      Sep. 18, 2014

Related U.S. Application Data

(60) Provisional application No. 61/801,561, filed on Mar. 15, 2013, provisional application No. 61/923,137, filed on Jan. 2, 2014.

(51) Int. Cl.
| | |
|---|---|
| *A61N 1/00* | (2006.01) |
| *A61N 1/36* | (2006.01) |
| *A61N 1/372* | (2006.01) |
| *G06F 3/0484* | (2013.01) |

(52) U.S. Cl.
CPC ..... *A61N 1/36128* (2013.01); *A61N 1/36185* (2013.01); *A61N 1/37247* (2013.01); *G06F 3/04847* (2013.01); *A61N 1/37241* (2013.01)

(58) Field of Classification Search
CPC .................................. A61N 1/37235–1/37247
See application file for complete search history.

(56) References Cited

U.S. PATENT DOCUMENTS

| | | | |
|---|---|---|---|
| 6,516,227 B1 | 2/2003 | Meadows et al. | |
| 6,895,280 B2 | 5/2005 | Meadows et al. | |
| 6,993,384 B2 | 1/2006 | Bradley et al. | |
| 2008/0163097 A1 | 7/2008 | Goetz et al. | |

(Continued)

FOREIGN PATENT DOCUMENTS

| | | |
|---|---|---|
| CN | 105120946 A | 12/2015 |
| CN | 105120946 B | 5/2017 |

(Continued)

OTHER PUBLICATIONS

U.S. Appl. No. 61/452,965, Neurostimulation System for Defining a Generalized Ideal Multipole Configuration, Inventor: Dongchul Lee et al., filed, Mar. 15, 2011.

(Continued)

*Primary Examiner* — Scott M. Getzow
(74) *Attorney, Agent, or Firm* — Schwegman Lundberg & Woessner, P.A.

(57) ABSTRACT

A neurostimulation system comprises at least one neurostimulation lead configured for being implanted within tissue. The neurostimulation lead(s) carries a plurality of electrodes capable of being arranged in a two-dimensional pattern. The neurostimulation system further comprises a neurostimulator configured for delivering electrical stimulation energy to the electrodes to create a volume of activation, and an external control device including a current steering direction control element capable of being rotated about an axis. The external control device is configured for prompting the neurostimulator to deliver the electrical stimulation energy to the electrodes in a manner that gradually translates the volume of activation in a specific direction, and for defining the specific direction in which the volume of activation is translated in response to rotation of the direction control element about the axis.

26 Claims, 6 Drawing Sheets

(56) References Cited

U.S. PATENT DOCUMENTS

| | | | |
|---|---|---|---|
| 2009/0287271 A1* | 11/2009 | Blum et al. | 607/45 |
| 2010/0010566 A1 | 1/2010 | Thacker et al. | |
| 2010/0121409 A1 | 5/2010 | Kothandaraman et al. | |
| 2011/0270358 A1* | 11/2011 | Davis et al. | 607/60 |
| 2011/0313268 A1 | 12/2011 | Kokones et al. | |
| 2012/0041518 A1* | 2/2012 | Kim et al. | 607/60 |
| 2012/0046715 A1 | 2/2012 | Moffitt et al. | |
| 2012/0109230 A1 | 5/2012 | Kothandaraman et al. | |
| 2012/0109257 A1 | 5/2012 | Yoo et al. | |
| 2012/0239109 A1 | 9/2012 | Lee | |
| 2012/0302912 A1 | 11/2012 | Moffitt et al. | |

FOREIGN PATENT DOCUMENTS

| | | | |
|---|---|---|---|
| JP | 2008011935 A | 1/2008 | |
| JP | 2016514023 A | 5/2016 | |
| JP | 6198927 B2 | 9/2017 | |
| WO | WO-2011133564 A1 | 10/2011 | |
| WO | WO-2014150001 | 9/2014 | |

OTHER PUBLICATIONS

U.S. Appl. No. 61/486,141, Neurostimulation System with On-Effector Programmer Control, Inventor: Chester Kim et al., filed, May 13, 2011.

U.S. Appl. No. 61/561,760, Technique for Linking Electrodes Together During Programming of Neurostimulation System, Inventor: Prakash Rao et al., filed, Nov. 18, 2011.

U.S. Appl. No. 61/576,924, Seamless Integration of Different Programming Modes for a Neurostimulator Programming System, Inventor: Sridhar Kothandaraman et al., filed, Dec. 16, 2011.

"International Application Serial No. PCT/US2014/021779, International Search Report dated Jun. 4, 2014", 4 pgs.

"Australian Application Serial No. 2014237614, Response filed Feb. 1, 2017 to First Examiner Report dated Apr. 12, 2016", 13 pgs.

"Chinese Application Serial No. 201480022554.X, Office Action dated Jul. 27, 2016", with English translation, 22 pgs.

"Chinese Application Serial No. 201480022554.X, Response filed Feb. 8, 2017 to Office Action dated Jul. 27, 2016", w/ Claims in English, 21 pgs.

"International Application Serial No. PCT/US2014/021779, International Preliminary Report on Patentability dated Sep. 24, 2015", 9 pgs.

"Japanese Application Serial No. 2016-500847, Office Action dated Sep. 20, 2016", with English translation, 5 pgs.

"Japanese Application Serial No. 2016-500847, Response filed Feb. 20, 2016 to Office Action dated Sep. 20, 2016", w/ Claims in English, 10 pgs.

"European Application Serial No. 14715748.1, Communication Pursuant to Article 94(3) EPC dated Sep. 21, 2018", 7 pgs.

\* cited by examiner

TECHNIQUES FOR CURRENT STEERING DIRECTIONAL PROGRAMMING IN A NEUROSTIMULATION SYSTEM

RELATED APPLICATIONS DATA

The present application claims the benefit under 35 U.S.C. §119 to U.S. Provisional Application Ser. No. 61/801,561, filed Mar. 15, 2013 and U.S. Provisional Application Ser. No. 61/923,137, filed Jan. 2, 2014, which applications are all incorporated herein by reference in their entirety.

FIELD OF THE INVENTION

The present inventions relate to tissue stimulation systems, and more particularly, to user interface for automated programming of leads of neurostimulation systems.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications, such as angina pectoralis and incontinence. Deep Brain Stimulation (DBS) has also been applied therapeutically for well over a decade for the treatment of refractory chronic pain syndromes, and DBS has also recently been applied in additional areas, such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl Corporation, Cleveland, Ohio, have been applied to restore some functionality to paralyzed extremities in spinal cord injury patients.

These implantable neurostimulation systems typically include one or more electrode carrying stimulation leads, which are implanted at the desired stimulation site, and a neurostimulator (e.g., an implantable pulse generator (IPG)) implanted remotely from the stimulation site, but coupled either directly to the stimulation lead(s) or indirectly to the stimulation lead(s) via a lead extension. The neurostimulation system may further include an external control device in the form of a remote control to remotely instruct the neurostimulator to generate electrical stimulation pulses in accordance with selected stimulation parameters.

Electrical stimulation energy may be delivered from the neurostimulator to the electrodes in the form of an electrical pulsed waveform. Thus, stimulation energy may be controllably delivered to the electrodes to stimulate neural tissue. The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include the amplitude, width, and rate of the electrical pulses provided through the electrode array. Each electrode combination, along with the electrical pulse parameters, can be referred to as a "stimulation parameter set."

With some related art neurostimulation systems, and in particular, those with independently controlled current or voltage sources, the distribution of the current to the electrodes (including the case where the neurostimulator acts as an electrode) may be varied, such that the current is supplied via numerous different electrode configurations. However, the electrodes of different configurations may provide current or voltage in different relative percentages of positive and negative current or voltage to create different electrical current distributions (i.e., fractionalized electrode combinations).

As briefly discussed above, a remote control can be used to instruct the neurostimulator to generate electrical stimulation pulses in accordance with the selected stimulation parameters. Typically, the stimulation parameters programmed into the neurostimulator can be adjusted by manipulating controls on the remote control to modify the electrical stimulation provided by the neurostimulator system to the patient. Thus, in accordance with the stimulation parameters programmed by the remote control, electrical pulses can be delivered from the neurostimulator to the stimulation electrode(s) to stimulate or activate a volume of tissue in accordance with a set of stimulation parameters, and provide the desired efficacious therapy to the patient. The best stimulus parameter set will typically be one that delivers stimulation energy to the volume of tissue that must be stimulated in order to provide the therapeutic benefit (e.g., treatment of pain), while minimizing the volume of non-target tissue that is stimulated.

However, the number of electrodes that are available, combined with the ability to generate a variety of complex stimulation pulses, presents a huge selection of stimulation parameter sets to the clinician or patient. For example, if the neurostimulation system to be programmed has an array of sixteen electrodes, millions of stimulation parameter sets may be available for programming into the neurostimulation system. Today, neurostimulation systems may include up to thirty-two electrodes, thereby exponentially increasing the number of stimulation parameter sets available for programming.

To facilitate selection among the large number of potential stimulation parameter sets, clinicians generally program the neurostimulator through a computerized programming system. The programming system can be a self-contained hardware/software system, or can be defined predominantly by software running on a standard personal computer (PC). The PC or custom hardware may actively control the characteristics of the electrical stimulation generated by the neurostimulator to allow the optimum stimulation parameters to be determined based on patient feedback (or other data), and to subsequently program the neurostimulator and optionally the remote control, with the optimum stimulation parameter set(s).

The Bionic Navigator®, available from Boston Scientific Neuromodulation Corporation, Valencia, Calif., is a related art computerized programming system for SCS. The Bionic Navigator® is a software package that operates on a suitable PC, and allows clinicians to program stimulation parameters into an external handheld programmer (referred to as a remote control). Each set of stimulation parameters, including fractionalized current distribution to the electrodes (as percentage cathodic current, percentage anodic current, or off), may be stored in both the Bionic Navigator® and the remote control, and combined into a stimulation program that can then be used to stimulate multiple regions within the patient.

Prior to creating the stimulation programs, the Bionic Navigator® may be operated by a clinician in a "manual mode" to manually select the percentage cathodic current and percentage anodic current flowing through the electrodes, or may be operated by the clinician in an "automated mode" to electrically "steer" the current along the implanted leads in real-time using a directional input device as an integral part of the user interface (e.g., joystick, button pad, group of keyboard arrow keys, and/or similar or equivalent controls), thereby facilitating the clinician's attempts to determine preferable or the most efficacious stimulation parameter sets that can then be stored and eventually combined into stimulation programs. The steering depends on the type of leads, the number of leads, and the arrangement of the electrodes implanted. Once a polarity and the amplitude (either as an absolute or a percentage) for the current or voltage on an active electrode is selected in a typical computerized programming system, the polarity and amplitude value associated with the electrodes may be presented on a display screen so as to be viewable by the user.

Despite the fact that computerized programming systems have been used to speed up the programming process, programming electrical stimulation systems using present-day computerized programming systems are relatively time-consuming. In the automated or current steering mode, the clinician manipulates the directional input device in predefined increments to adjust a current stimulation field generated due to the realignment of the stimulation parameters, such as amplitude of the current associated with the electrodes, from one preset value to the next preset value. If the difference between the desired preset value and the existing preset value is large, then the number of manipulations of the input directional device may be high, which delays the process of selecting optimized stimulation parameter settings.

Also for the automated or current steering mode, the inherent limitation of directional input device restricts the user's ability to maneuver the device minutely or with complete freedom, and thus the user may fail to benefit from preferable or optimal stimulation settings.

There, thus, remains a need to provide a simplified and efficient directional current steering programming of the electrodes of neurostimulation system.

SUMMARY OF THE INVENTION

In accordance with one aspect of the present inventions, an external control device for use with a two-dimensional array of electrodes implanted within tissue and a neurostimulator capable of delivering electrical stimulation energy to the electrodes to create a volume of activation is provided. The external control device comprises a user interface including a current steering initiation control element and a current steering direction control element (e.g., a knob or wheel) capable of being rotated about an axis. In an optional embodiment, the user interface includes a display screen configured for displaying the direction control element as a graphical element configured for being rotated by a pointing element.

The external control device further comprises a controller/processor configured for, in response to actuation of the initiation control element, generating a series of different combinations of the electrodes (e.g., fractionalized electrode combinations) in a manner that the volume of activation gradually translates in a specific direction when the electrical stimulation energy is delivered to the different electrode combinations. In one embodiment, the controller/processor is configured for translating an ideal multipole relative to the electrode array in response actuation of the initiation control element, in which case, the different electrode combinations emulate the translation of the ideal multipole. In an optional embodiment, the user interface includes a display screen configured for displaying the volume of activation relative to the electrode array, in which case, the controller/processor will be configured for estimating the volume of activation based on the different electrode combinations.

The controller/processor is further configured for, in response to rotation of the direction control element about the axis, defining the specific direction in which the volume of activation is translated. In one embodiment, the controller/processor is configured for defining the specific direction in response to the actuation of the direction control element prior to the generation of the series of different electrode combinations. In another embodiment, the controller/processor is configured for defining the specific direction in response to the actuation of the direction control element while the series of different electrode combinations are being generated.

The direction control element may include an arrow that indicates the specific direction in which the volume of activation is translated. The direction control element may be capable of being selectively rotated about the axis in a clockwise direction and a counterclockwise direction, in which case, the controller/processor will be configured for, in response to rotation of the direction control element about the axis in the clockwise direction, adjusting the direction in which the volume of activation is translated in a first direction, and in response to rotation of the direction control element about the axis in the counterclockwise direction, adjusting the direction in which the volume of activation is translated in a second direction opposite to the first direction.

The external control device further comprises output circuitry (e.g., telemetry circuitry) configured for transmitting the different electrode combinations to the neurostimulator. The external control device may comprise a housing containing the user interface, controller/processor, and output circuitry.

In an optional embodiment, the user interface further includes a current steering speed control element, in which case, the controller/processor is configured for, in response to actuation of the speed control element, modifying the manner in which the electrode combinations are generated to adjust the speed at which the volume of activation translates. The speed control element may have an acceleration sub-element and a deceleration sub-element, in which case, the controller/processor may be configured for, in response to actuation of the acceleration sub-element, modifying the manner in which the electrode combinations are generated to increase the speed at which the volume of activation translates, and in response to actuation of the deceleration sub-element, modifying the manner in which the electrode combinations are generated to decrease the speed at which the volume of activation translates. In another optional embodiment, the user interface further includes a current steering time control element, in which case, the controller/processor is configured for, in response to actuation of the time control element, generating the series of different combinations of the electrodes for a specified time period, such that the translation of the volume of activation ceases when the time period has elapsed.

In accordance with a second aspect of the present inventions, a neurostimulation system is provided. The neurostimulation system comprises at least one neurostimulation lead configured for being implanted within tissue. The neurostimulation lead(s) carries a plurality of electrodes capable of being arranged in a two-dimensional pattern. The neurostimulation system further comprises a neurostimulator configured for delivering electrical stimulation energy to the electrodes to create a volume of activation.

The neurostimulation system further comprises an external control device including a current steering direction control element (e.g., a knob or wheel) capable of being rotated about an axis. In an optional embodiment, the user interface includes a display screen configured for displaying the direction control element as a graphical element configured for being rotated by a pointing element. The external control device is configured for prompting the neurostimulator to deliver the electrical stimulation energy to the electrodes in a manner that gradually translates the volume of activation in a specific direction, and for defining the specific direction in which the volume of activation is translated in response to rotation of the direction control element about the axis. In one embodiment, the external control device is configured for defining the specific direction in response to the actuation of the direction control element prior to the generation of the series of different electrode combinations. In another embodiment, the external control device is configured for defining the specific direction in response to the actuation of the direction control element while the series of different electrode combinations are being generated.

The direction control element may include an arrow that indicates the specific direction in which the volume of activation is translated. The direction control element may be capable of being selectively rotated about the axis in a clockwise direction and a counterclockwise direction, in which case, the external control device will be configured for, in response to rotation of the direction control element about the axis in the clockwise direction, adjusting the direction in which the volume of activation is translated in a first direction, and in response to rotation of the direction control element about the axis in the counterclockwise direction, adjusting the direction in which the volume of activation is translated in a second direction opposite to the first direction. In an optional embodiment, the external control device is configured for adjusting the speed at which the volume of activation translates. In another optional embodiment, the external control device is configured for defining a time period and automatically ceasing translation of the volume of activation when the time period has elapsed.

In accordance with a third aspect of the present invention, another external control device for use with a two-dimensional array of electrodes implanted within tissue and a neurostimulator capable of delivering electrical stimulation energy to the electrodes to create a volume of activation is provided. The external control device comprises a user interface including a current steering speed control element. In an optional embodiment, the user interface includes a display screen configured for displaying the current steering speed control element as a graphical element configured for being rotated by a pointing element.

The external control device further comprises a controller/processor configured for generating a series of different combinations (e.g., fractionalized electrode combinations) of the electrodes in a manner that the volume of activation gradually translates in a specific direction when the electrical stimulation energy is delivered to the different electrode combinations, and in response to actuation of the speed control element, modifying the manner in which the electrode combinations are generated to adjust the speed at which the volume of activation translates.

The external control device further comprises an output circuitry (e.g., telemetry circuitry) configured for transmitting the different electrode combinations to the neurostimulator. The external control device may comprise a housing containing the user interface, controller/processor, and output circuitry.

In an optional embodiment, the user interface further includes a current steering initiation control element and a current steering direction control element, in which case, the controller/processor will be configured for, in response to actuation of the initiation control element, generating the series of different electrode combinations in a manner that the volume of activation gradually translates in a specific direction when the electrical stimulation energy is delivered to the different electrode combinations, and in response to actuation of the direction control element, defining the specific direction in which the volume of activation is translated.

In one embodiment, the controller/processor is configured for translating an ideal multipole relative to the electrode array in response actuation of the initiation control element, in which case, the different electrode combinations emulate the translation of the ideal multipole. In an optional embodiment, the user interface includes a display screen configured for displaying the volume of activation relative to the electrode array, in which case, the controller/processor will be configured for estimating the volume of activation based on the different electrode combinations.

The speed control element may have an acceleration sub-element and a deceleration sub-element, in which case, the controller/processor may be configured for, in response to actuation of the acceleration sub-element, modifying the manner in which the electrode combinations are generated to increase the speed at which the volume of activation translates, and in response to actuation of the deceleration sub-element, modifying the manner in which the electrode combinations are generated to decrease the speed at which the volume of activation translates. In another optional embodiment, the user interface further includes a current steering time control element, in which case, the controller/processor is configured for, in response to actuation of the time control element, generating the series of different combinations of the electrodes for a specified time period, such that the translation of the volume of activation ceases when the time period has elapsed.

In accordance with a fourth aspect of the present inventions, another neurostimulation system is provided. The neurostimulation system comprises at least one neurostimulation lead configured for being implanted within tissue. The neurostimulation lead(s) carries a plurality of electrodes capable of being arranged in a two-dimensional pattern. The neurostimulation system further comprises a neurostimulator configured for delivering electrical stimulation energy to the electrodes to create a volume of activation.

The neurostimulation system further comprises an external control device configured for prompting the neurostimulator to deliver the electrical stimulation energy to the electrodes in a manner that gradually translates the volume of activation in a specific direction, and for adjusting the speed at which the volume of activation translates, which may be performed in response to a user input. In an optional embodiment, the external control device is further configured for defining the specific direction in which the volume of activation is translated in response to a use input. In another optional embodiment, the external control device is further configured for defining a time period and automatically ceasing translation of the volume of activation when the time period has elapsed.

Other and further aspects and features of the disclosed embodiments will be evident from reading the following detailed description of the embodiments, which are intended to illustrate, not limit, the invention.

BRIEF DESCRIPTION OF THE DRAWINGS

The drawings illustrate the design and utility of various embodiments of the present invention, in which similar elements are referred to by common reference numerals. In order to better appreciate how the above-disclosed and other advantages and objects of the various embodiments are obtained; a more particular explanation is provided below with reference to specific embodiments thereof, which are illustrated in the accompanying drawings. However, these drawings depict only some embodiments of the invention, and are not therefore to be considered limiting of its scope. A brief description of the drawings is provided below.

DETAILED DESCRIPTION

The following description is provided in the context of Spinal Cord Stimulation (SCS) systems. However, it is to be understood that, while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, and/or in any other neural stimulator configured to treat urinary incontinence, sleep apnea, shoulder sublaxation, headache, etc.

Figure 1:
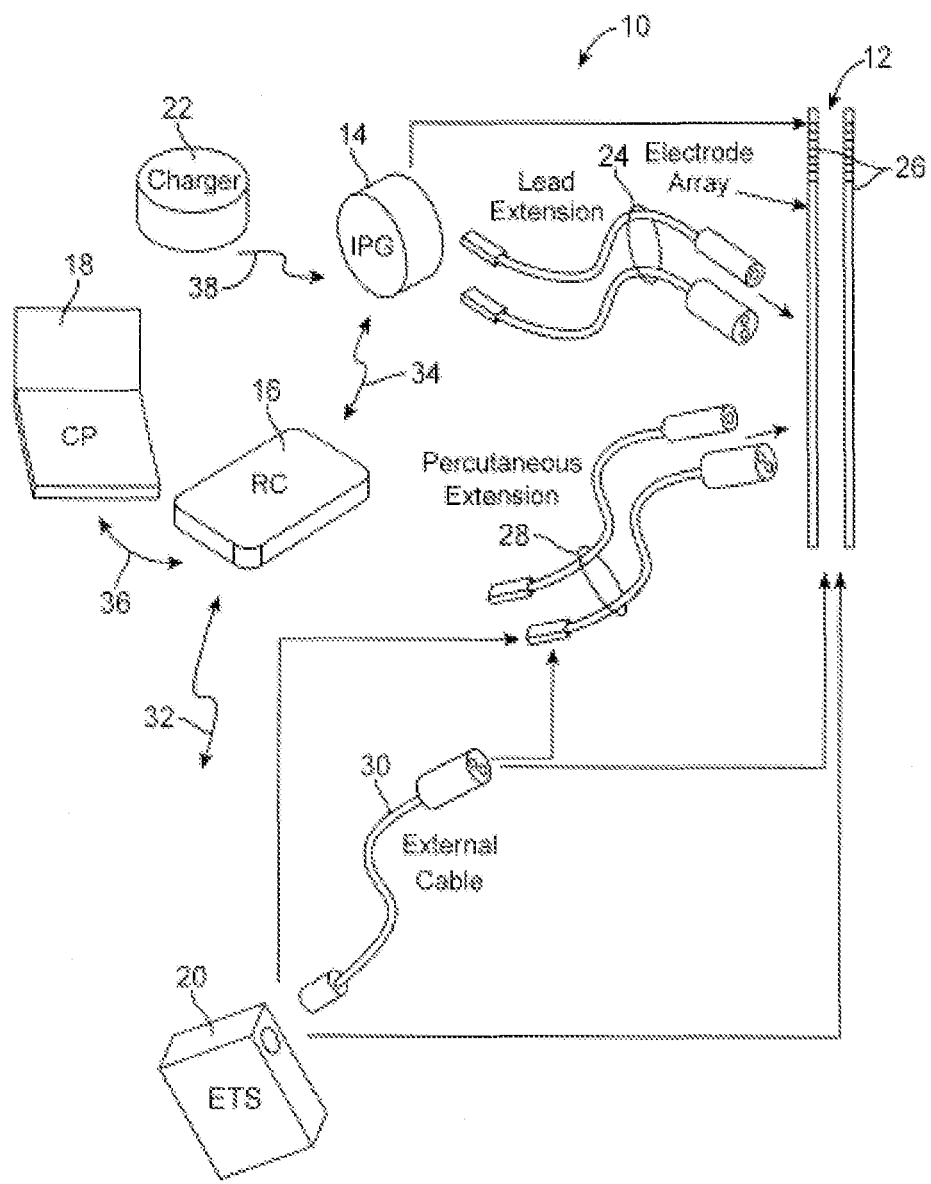
FIG. 1 is a plan view of a Spinal Cord Stimulation (SCS) system constructed in accordance with one embodiment of the present disclosure.

FIG. 1 shows an exemplary SCS system 10 that generally includes multiple (in this case, two) implantable neurostimulation leads 12, an Implantable Pulse Generator (IPG) 14, an external Remote Controller (RC) 16, a clinician's programmer (CP) 18, an external trial stimulator (ETS) 20, and an external charger 22.

The IPG 14 is physically connected via one or more percutaneous lead extensions 24 to the neurostimulation leads 12, which carry multiple electrodes 26 arranged in an array. In the illustrated embodiment, the neurostimulation leads 12 are percutaneous leads, and to this end, the electrodes 26 are arranged in-line along the neurostimulation leads 12. Depending upon the desired therapy, the electrodes 26 may be implanted within the tissue in more than one dimension. Alternatively, a surgical paddle lead can be used in place of, or in addition to, the percutaneous leads. As will be described in further detail below, the IPG 14 includes pulse generation circuitry that delivers electrical stimulation energy in the form of a pulsed electrical waveform (i.e., a temporal series of electrical pulses) to the electrodes 26 in an electrode array in accordance with a set of stimulation parameters.

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrodes 26, in accordance with a set of stimulation parameters. A significant difference between the ETS 20 and the IPG 14 is that the ETS 20 is a non-implantable device that is used on a trial basis, after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and the neurostimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and the ETS 20 in the operating room and in follow-up sessions.

The CP 18 may perform this function by indirectly communicating with the IPG 14 or the ETS 20, through the RC 16, via an IR communications link 36. Alternatively, the CP 18 may directly communicate with the IPG 14 or the ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18). In an embodiment, the CP 18 may include a user interface, which has a current steering initiation control element and a current steering direction control element, which is capable of being rotated about an axis.

The external charger 22 is a portable device used to transcutaneously charge the IPG 14 via an inductive link 38. For purposes of brevity, the details of the external charger 22 will not be described herein. Once the IPG 14 has been programmed, and its power source has been charged by the external charger 22 or otherwise replenished, the IPG 14 may function as programmed without the RC 16 or the CP 18 being present.

For purposes of brevity, the details of the IPG 14, the ETS 20, and the external charger 22 will not be described herein. Details of exemplary embodiments of these devices are disclosed in U.S. Pat. No. 6,895,280, which is expressly incorporated herein by reference in its entirety.

Figure 2:
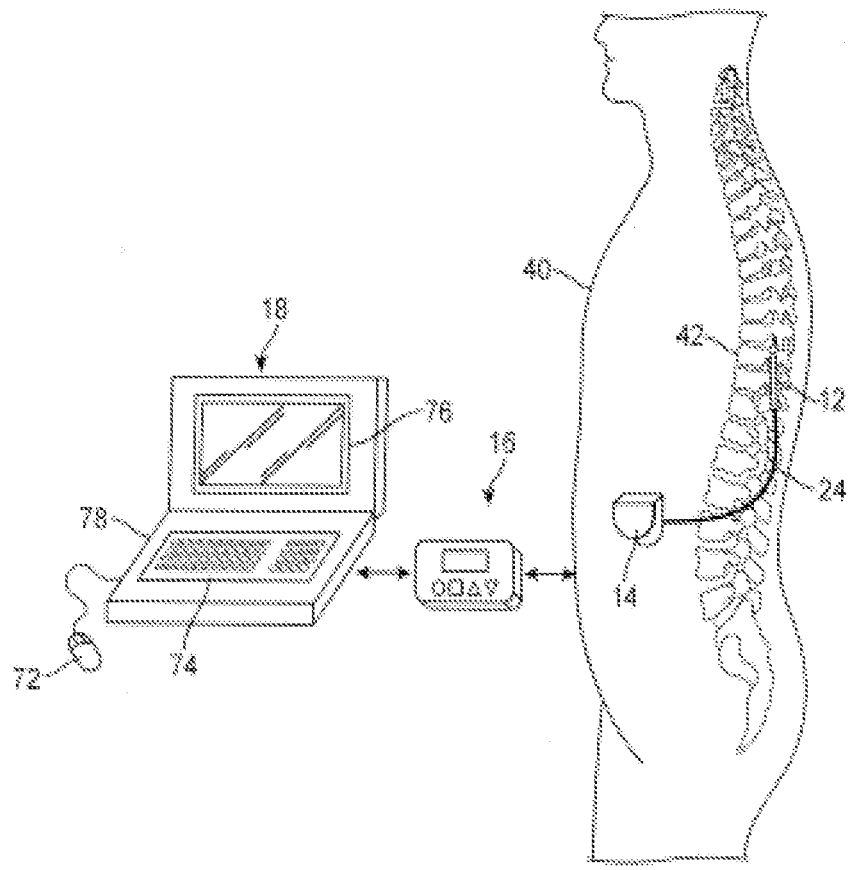
FIG. 2 is a perspective view of the arrangement of the SCS system of FIG. 1 with respect to a patient.

As shown in FIG. 2, the neurostimulation leads 12 are implanted within the spinal column 42 of a patient 40. A beneficial or even preferred placement of the neurostimulation leads 12 is adjacent, i.e., resting over, the spinal cord area to be stimulated. Due to the lack of space near the location where the neurostimulation leads 12 exit the spinal column 42, the IPG 14 is generally implanted in a surgically made pocket, either in the abdomen or above the buttocks of the patient. The IPG 14 may also be implanted in other locations of the patient's body. The lead extensions 24 facilitate locating the IPG 14 away from the exit point of the neurostimulation leads 12. As shown in the FIG. 2, the CP 18 communicates with the IPG 14 via the RC 16.

Figure 3:
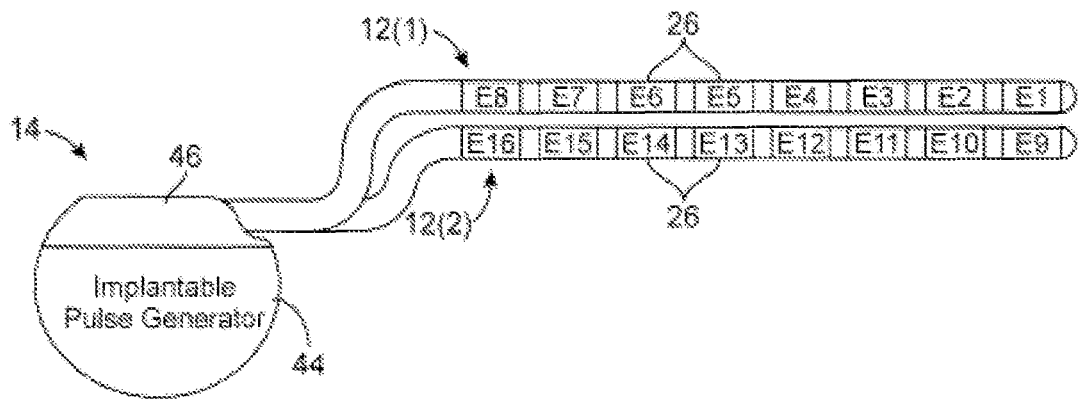
FIG. 3 is a profile view of an implantable pulse generator (IPG) and percutaneous leads used in the SCS system of FIG. 1.

Features of the neurostimulation leads 12 and the IPG 14 are briefly described below with reference to FIG. 3. One of the neurostimulation leads 12(1) has eight electrodes 26 (labeled E1-E8), and the other neurostimulation lead 12(2) has eight electrodes 26 (labeled E9-E16). The actual number and shape of leads and arrangement of electrodes may vary according to the intended application. The IPG 14 comprises an outer case 44 for housing the electronic and other components (described in further detail below). The outer case 44 is composed of an electrically conductive, biocompatible material, such as titanium, and forms a hermetically sealed compartment in which the internal electronics are protected from the body tissue and fluids. In some cases, the outer case 44 may serve as an electrode. The IPG 14 further comprises a connector 46 to which the proximal ends of the neurostimulation leads 12 mate in a manner that electrically couples the electrodes 26 to the internal electronics (described in further detail below) within the outer case 44. To this end, the connector 46 includes one or more ports (two ports 48 for two percutaneous leads) for receiving the proximal end(s) of the neurostimulation leads 12. In the case where the lead extensions 24 are used, the ports 48 may instead receive the proximal ends of such lead extensions 24.

The IPG 14 includes a battery and pulse generation circuitry that delivers the electrical stimulation energy in the form of a pulsed electrical waveform to the electrodes 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrodes 26), pulse width (measured in microseconds), and pulse rate (measured in pulses per second).

Electrical stimulation will occur between two (or more) activated electrodes, one of which may be the IPG outer case 44. Stimulation energy may be transmitted to the tissue in a monopolar or multipolar (e.g., bipolar, tripolar, etc.) fashion. Monopolar stimulation occurs if a selected one of the lead electrodes 26 is activated along with the outer case 44 of the IPG 14, so that stimulation energy is transmitted between the selected electrode 26 and the outer case 44. Bipolar stimulation occurs if two of the lead electrodes 26 are activated as anode and cathode, so that stimulation energy is transmitted between the selected electrodes 26. For example, electrode E3 on the first lead 12(1) may be activated as an anode, at the same time that electrode E11 on the second lead 12(2) is activated as a cathode. Tripolar stimulation occurs if three of the lead electrodes 26 are activated, two as anodes and the remaining one as a cathode, or two as cathodes and the remaining one as an anode. For example, electrodes E4 and E5 on the first lead 12(1) may be activated as anodes at the same time that electrode E12 on the second lead 12(2) is activated as a cathode.

The IPG 14 can individually control the magnitude of electrical current flowing through each of the electrodes. In this case, it is beneficial or even preferred to have a current generator, wherein individual current-regulated outputs from independent current sources for each electrode 26 may be selectively generated. Although this system may be beneficial or even optimal for reasons discussed above, other stimulators may be used with the invention, such as stimulators having voltage-regulated outputs. While individually programmable electrode 26 are beneficial or even optimal to achieve fine control, a single output source switched across electrodes 26 may also be used, although with less fine control in programming. Mixed current and voltage-regulated devices may also be used with the various embodiments. Further details of the structure and function of IPGs are provided more fully in U.S. Pat. Nos. 6,516,227 and 6,993,384, which are expressly incorporated herein by reference in their entireties.

Rather than an IPG, the SCS system 10 may alternatively utilize an implantable receiver-stimulator (not shown) connected to the neurostimulation leads 12. In this case, the power source, e.g., a battery, for powering the implanted receiver, as well as control circuitry to command the receiver-stimulator, is contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 4:
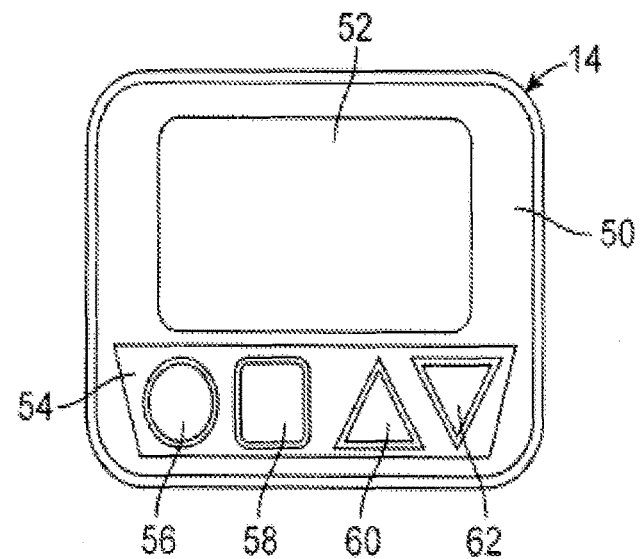
FIG. 4 is front view of a remote control (RC) used in the SCS system of FIG. 1.

FIG. 4 shows one exemplary embodiment of an RC 16. As previously discussed, the RC 16 is capable of communicating with the IPG 14, the CP 18, or the ETS 20. The RC 16 comprises a casing 50, which houses internal components (including a printed circuit board (PCB)), as well as a lighted display screen 52 and a button pad 54 provided at the exterior of the casing 50. The display screen 52 is a lighted flat panel display screen, and the button pad 54 comprises a membrane switch with metal domes positioned over a flex circuit, and a keypad connector connected directly to a PCB. However, embodiments are intended to cover any other applicable structures. For example, in another embodiment, the display screen 52 has touch screen capabilities.

The button pad 54 can include multiple buttons 56, 58, 60, and 62, which allow the IPG 14 to be turned ON and OFF, provide for the adjustment or setting of stimulation parameters within the IPG 14, and provide for selection between screens. The button 56 serves as an ON/OFF button that can be actuated to turn the IPG 14 ON and OFF. The button 58 serves as a select button that allows the RC 16 to switch between screen displays and/or parameters. The buttons 60 and 62 serve as up/down buttons that can be actuated to increment or decrement any of stimulation parameters of the pulse generated by the IPG 14, including pulse amplitude, pulse width, and pulse rate. For example, the selection button 58 can be actuated to place the RC 16 in a "Pulse Amplitude Adjustment Mode," during which the pulse amplitude can be adjusted via the up/down buttons 60, 62, a "Pulse Width Adjustment Mode," during which the pulse width can be adjusted via the up/down buttons 60, 62, and a "Pulse Rate Adjustment Mode," during which the pulse rate can be adjusted via the up/down buttons 60, 62. Alternatively, the dedicated up/down buttons 60, 62 can be provided for each stimulation parameter. The buttons 56, 58, 60 and 62 are used for the manual adjustment mode but may be customized to operate in automatic current steering mode. Rather than using up/down buttons 60, any other type of actuator, such as a dial, slider bar, or keypad, can be used to increment or decrement the stimulation parameters in the manual mode of programming the IPG 14, where the stimulation parameters like electrode selection are adjusted to deliver beneficial or even optimal therapy through the selected electrodes. Further details of the functionality and internal components of the RC 16 are disclosed in U.S. Pat. No. 6,895,280, which has previously been incorporated herein by reference.

Figure 5:
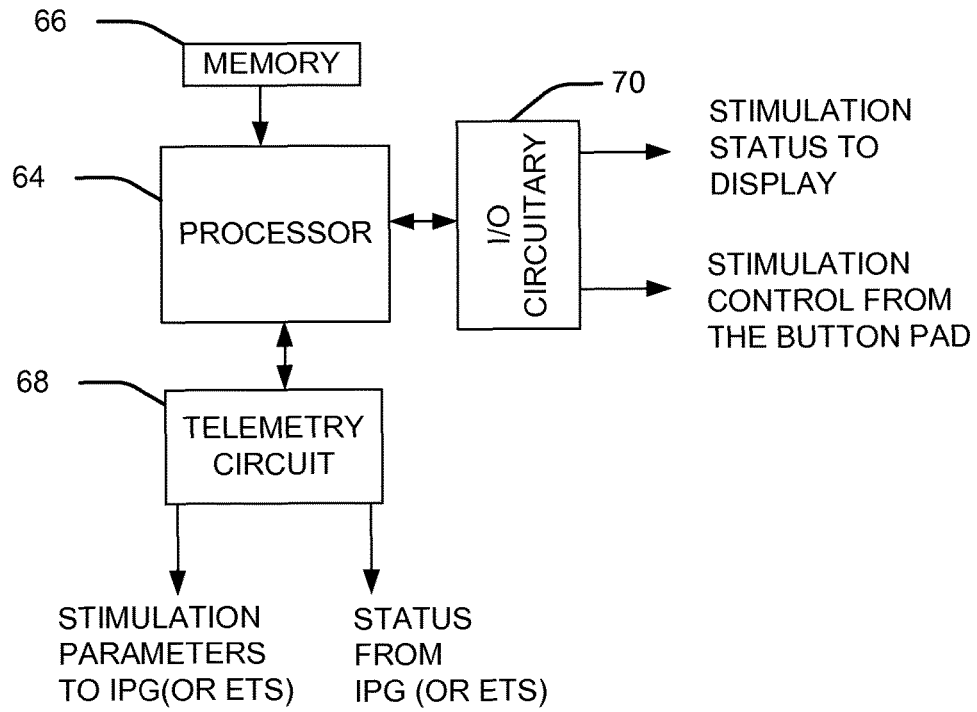
FIG. 5 is a block diagram of the internal components of the RC of FIG. 4.

The internal components of an exemplary RC 16 are described below with reference to FIG. 5. The RC 16 generally includes a processor 64 (e.g., a microcontroller), a programmable memory 66 that stores an operating program for execution by the processor 64, as well as stimulation parameter sets in a navigation table (described below), a telemetry circuitry 68 for outputting stimulation parameters to the IPG 14 and receiving status information from the IPG 14, and an input/output circuitry 70 for receiving stimulation control signals from the button pad 54 and transmitting status information to the display screen 52 (shown in FIG. 4). As well as controlling other functions of the RC 16, which will not be described herein for purposes of brevity, the processor 64 generates new stimulation parameter sets in response to the user operation of the button pad 54. These new stimulation parameter sets are then transmitted to the IPG 14 via the telemetry circuitry 68. Further details of the functionality and internal components of the RC 16 are disclosed in U.S. Pat. No. 6,895,280, which has previously been incorporated herein by reference.

As briefly discussed above, the CP 18 greatly simplifies the programming of multiple electrode combinations, allowing the user (e.g., the physician or clinician) to readily determine the desired stimulation parameters to be programmed into the IPG 14, as well as the RC 16. Thus, modification of the stimulation parameters in the programmable memory 66 of the RC 16 as well in the IPG 14 after implantation is performed by a user using the CP 18, which can directly communicate with the IPG 14 or indirectly communicate with the IPG 14 via the RC 16.

As shown in FIG. 2, the overall appearance of the CP 18 can be that of a laptop personal computer (PC), and in fact, may be implanted using a PC that has been appropriately configured to include a directional programming device and programmed to perform the functions described herein. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient feedback, and for subsequently programming the IPG 14 with the optimum stimulation parameters.

The CP 18 includes a mouse 72, a keyboard 74, and a display screen 76 housed in a case 78, to enable the user to perform the above operations. The display screen 76 is shown as a conventional screen in FIG. 2. However, embodiments can include other or additional elements to perform the above operations. For example, in addition to, or in lieu of, the mouse 72, other directional programming devices may be used, such as a trackball, touchpad, or joystick. Alternatively, instead of being conventional, the display screen 76 may be a digitizer screen, such as a touchscreen (not shown), and may be used in conjunction with an active or passive digitizer stylus/finger touch. Further details discussing the use of a digitizer screen for programming are set forth in U.S. Provisional Patent Application Ser. No. 61/561,760, entitled "Technique for Linking Electrodes Together during Programming of Neurostimulation System," which is expressly incorporated herein by reference in its entirety.

Figure 6:
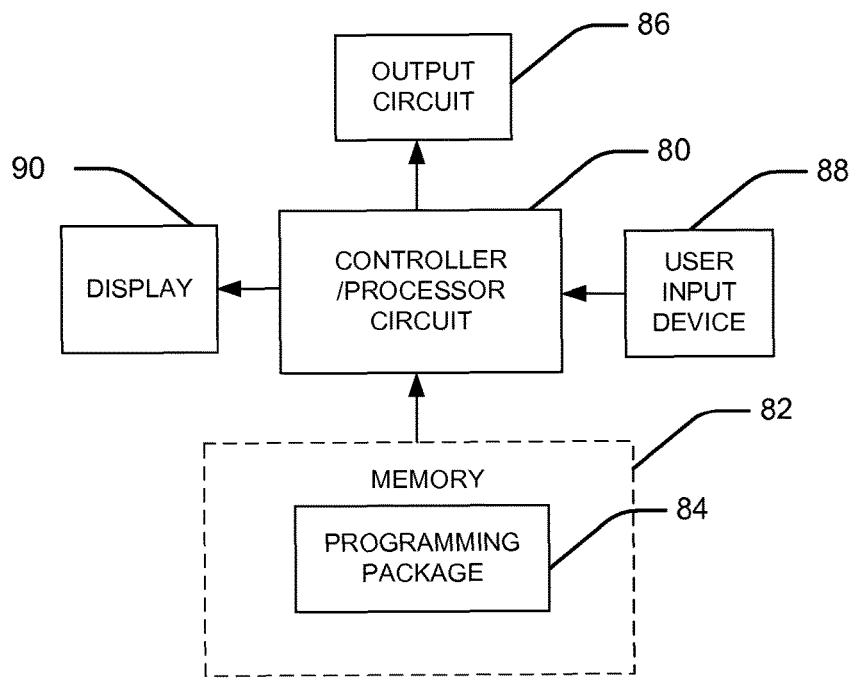
FIG. 6 is a block diagram of the internal components of a clinician's programmer (CP) used in the SCS system of FIG. 1.

As shown in FIG. 6, the CP 18 generally includes a controller/processor 80 (e.g., a central processor unit (CPU)) and a memory 82 that stores a stimulation programming package 84, which can be executed by the controller/processor 80 to allow the user to program the IPG 14 and the RC 16. The CP 18 further includes output circuitry 86 (e.g., via the telemetry circuitry of the RC 16) for downloading stimulation parameters to the IPG 14 and the RC 16, and for uploading stimulation parameters already stored in the memory 66 of the RC 16, via the telemetry circuitry 68 of the RC 16. In addition, a user input device 88, such as the mouse 72 or the keyboard 74, is attached to provide user commands. Although the controller/processor 80 is shown in FIG. 6 as a single device, the processing functions and controlling functions can be performed by a separate controller and a processor.

Execution of the programming package 84 by the controller/processor 80 provides a multitude of display screens 90 that can be navigated through. These display screens 90 allow the clinician, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical stimulation energy output by the neurostimulation leads 12, and select and program the IPG 14 with stimulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Neurostimulation Electrodes," which are expressly incorporated herein by reference.

Figure 7:
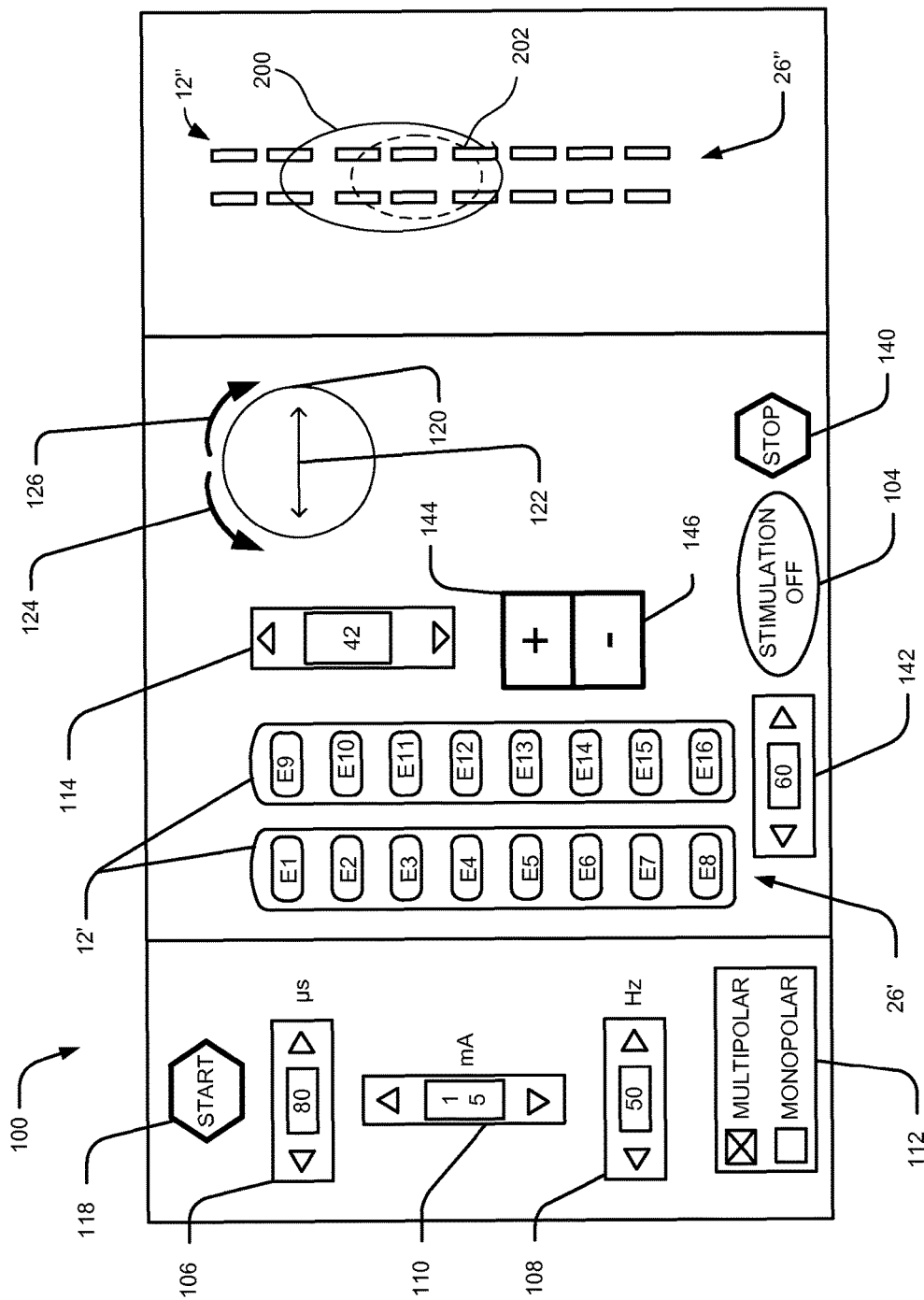
FIG. 7 is a plan view of an exemplary user interface of the CP of FIG. 6, for automated current steering programming of the IPG of FIG. 3, in accordance with a first embodiment of the present disclosure.

As one example, and with reference to FIG. 7, an exemplary programming screen 100 generated by the CP 18 to allow a user to program the IPG 14 will now be described. The programming screen 100 includes various control elements described below that can be actuated to perform various control functions.

A pointing element may be used to graphically touch the control elements to perform the actuation event. Therefore, in the case of the digitizer touch screen, the pointing element will be a physical pointing element (e.g., a finger or active or passive stylus) that can be used to tap the screen on a respective graphical control element, or otherwise brought into proximity with respect to the graphical control element.

In case of a conventional screen, the pointing element will be a virtual pointing element (e.g., a cursor) that can be used to graphically click on the respective control element.

The programming screen 100 includes stimulation on/off control 104 that can be alternately actuated to initiate or cease the delivery of electrical stimulation energy from the IPG 14 via the electrodes 26. The programming screen 100 further includes various stimulation parameter controls that can be operated by the user to manually adjust stimulation parameters for a selected electrode combination. In particular, the programming screen 100 includes a pulse width adjustment control 106 (expressed in microseconds (µs)), a pulse rate adjustment control 108 (expressed in Hertz (Hz)), and a pulse amplitude adjustment control 110 (expressed in milli-amperes (mA)). Each of the controls 106, 108, 110 includes a first arrow that may be actuated to decrease the value of the respective stimulation parameter, and a second arrow that may be actuated to increase the value of the respective stimulation parameter. Further, each of the controls 106, 108, 110 may include a display to indicate the present value of the respective parameter. For example, the present value of the pulse width adjustment control is "80 µs", the present value of the pulse rate adjustment control is "50 Hz" and the present value of pulse amplitude adjustment control is "15 mA".

To enable a user to select individual electrodes, the programming screen 100 displays graphical representations of the neurostimulation leads 12' including the electrodes 26'. Each electrode representation 26' can take the form of a closed geometric figure, such as a rectangle, circle, ellipse, trapezoid etc. The electrode representations 26' can be actuated with a physical pointing device, or otherwise clicked with a virtual pointing device, multiple times to switch the corresponding active electrodes 26 between an on-state, which includes either positive polarity (anode) or a negative polarity (cathode), and an off-state. In essence, the electrode representations 26' operate as the graphical control elements, the actuations of which prompt the controller/processor 80 to assign the polarities to the selected electrodes 26. In alternative embodiments, control elements separate from the electrode representations 26' may be used to change the polarity of the selected electrodes 26.

To enable selection between a multipolar configuration and a monopolar configuration, the programming screen 100 also includes a multipolar/monopolar stimulation selection control 112, which includes check boxes that can be alternately actuated by the user to selectively provide multipolar or monopolar stimulation. If a multipolar electrode arrangement is desired, at least one of the electrodes E1-E16 will be selected as an anode (+), and at least one other of the electrodes E1-E16 will be selected as a cathode (−). If a monopolar electrode arrangement is desired, none of the electrodes E1-E16 will be selected as an anode (+), and thus the electrode representations 26' can only be actuated to toggle the corresponding electrode 26 between a cathode (−) and off (0).

The programming screen 100 further includes an electrode-specific current adjustment control 114 that can be manipulated to independently vary stimulation amplitude values for the electrodes E1-E16. In particular, for each electrode selected to be activated as either a cathode or anode, the clinician can actuate the upper arrow of the control 114 to incrementally increase the absolute value of the stimulation amplitude of the selected electrode, and the clinician can actuate the lower arrow of the control 114 to incrementally decrease the absolute value of the stimulation amplitude of the selected electrode. The control 114 also includes an indicator that provides an alphanumeric indication of the stimulation amplitude currently assigned to the selected electrode. In an alternative embodiment, non-alphanumeric indicators, such as different colors, different color luminance, different patterns, different textures, different graphical objects, etc., can be used to indicate the stimulation amplitude presently assigned to the selected electrodes, as discussed in U.S. patent application Ser. No. 13/200,629, entitled "Neurostimulation System and Method for Graphically Displaying Electrode Stimulation Values," which is expressly incorporated herein by reference in its entirety.

In addition, the stimulation amplitude values may be fractionalized electrical current values (i.e., percentage of electric current), such that the summation of values for each polarization is 100. However, in alternative embodiments, the stimulation amplitude values may be normalized current or voltage values (e.g., 1-10), absolute current or voltage values (e.g., mA or V), etc. Furthermore, the stimulation amplitude values may be parameters that are a function of current or voltage, such as charge (current amplitude×pulse width) or charge injected per second (current amplitude× pulse width×rate (or period)).

In alternative embodiments, a stimulation amplitude adjustment control (not shown) may appear next to the electrode representations 26' that has been actuated, as described in U.S. patent application Ser. No. 13/200,629, which has been previously incorporated herein by reference, or may be superimposed over the electrode representations 26' that has been actuated, as described in U.S. Provisional Patent Application Ser. No. 61/486,141, entitled "Neurostimulation System with On-Effector Programmer Control," which is expressly incorporated herein by reference in its entirety. In another embodiment, the stimulation amplitude values may be typed or written into a graphical data entry symbol associated with an electrode (e.g., adjacent, next to and/or superimposed over the electrode representations 26').

The programming screen 100 facilitates automated current steering; for example, by allowing the user to switch between a manual mode using the electrode selection and current adjustment techniques described above and an automated current steering mode. The automated current steering mode can be implemented through techniques, such as, (1) an electronic trolling ("e-troll") mode that quickly sweeps the electrode array using a limited number of electrode configurations to gradually move a cathode in bipolar stimulation, and (2) a Navigation programming mode that finely tunes and optimizes stimulation coverage for patient comfort using a wide number of electrode configurations, as described in U.S. Provisional Patent Application Ser. No. 61/576,924, entitled "Seamless Integration of Different Programming Modes for a Neurostimulator Programming System," which is expressly incorporated herein by reference in its entirety.

These current steering techniques may be performed, e.g., using virtual target poles to steer the current within the electrode array, as described in U.S. Provisional Patent Application Ser. No. 61/452,965, entitled "Neurostimulation System for Defining a Generalized Virtual Multipole," which is expressly incorporated herein by reference. Alternatively, steering tables may be utilized to execute these techniques and steer the current within the electrode array, as described in U.S. patent application Ser. No. 12/614,942, entitled "System and Method for Determining Appropriate Steering Tables for Distributing Stimulation Energy Among Multiple Neurostimulation Electrodes," which is also expressly incorporated herein by reference. More pertinent to the present disclosure, the current steering programming is enabled through a current steering initiation control element "start" button 118 and a current steering direction control element "knob" 120 capable of being rotated about an axis.

The knob 120 includes a bi-directional arrow 122 positioned within the circumferential periphery of the knob 120. The bi-directional arrow 122 representation enables exact visual indication of the direction, specified at that instant, in which the electric stimulation current is being steered, with respect to the axis of the leads 12 and the electrodes 26. In an alternative embodiment, the exact direction of the steering is visually highlighted by a higher luminance of the arrow head of the bi-directional arrow 122 that is aligned towards the direction in which the steering is specified by the user, as compared to the lumen intensity of the opposite arrow head of the bi-directional arrow 122.

The programming screen 100 also includes graphical representations of a pair of single directional arrows 124, 126, positioned and aligned along the outer circumferential periphery of the knob 120. Alternatively, the arrows 124, 126 may be positioned inside the knob 120. The arrows 124 and 126 are represented to be curved in opposite directions to each other, to indicate counter-clockwise and clockwise directions respectively. The arrows 124 and 126, when actuated, emulate the functionality provided by rotating the knob 120, in small increments. For example, when the arrow 124 is actuated, the knob 120 rotates in counter-clockwise direction and when the arrow 126 is actuated, the knob 120 rotates in clockwise direction, proportionate to the amount of actuation applied to the respective arrows. The arrows 124, 126 can be actuated in a single continuous or multiple discreet times to impart the knob 120, with the desired degree of rotation.

Further, the programming screen 100 displays a two-dimensional graphical rendering of the leads 12" relative to a graphical representation of the anatomical structure 200 that is preferably the stimulation target. The leads 12" include the electrodes 26". Each electrode representation 26' may take the form of a closed geometric figure, such as a rectangle, circle, ellipse, trapezoid, etc. Based on the current stimulation parameter set, the controller/processor 80 computes an estimate of a resulting Volume of Activation (VOA) 202, and generates display signals that prompt the display screen 76 to display a graphical representation of the VOA 202 with the graphical electrode array 26" and graphical anatomical structure 200. In the preferred embodiment, the graphical VOA 202 is superimposed over the graphical anatomical structure 200. In response to actuation of the start button 118, the controller/processor 80 is configured to steer current by generating a series of different combinations of the electrodes in a manner that the VOA 202 gradually translates in a specific direction when the electrical stimulation energy is delivered to the different electrode combinations. Further, the controller/processor 80 is configured for defining the specific direction of current steering in which the VOA 202 is translated, in response to rotation of the knob 120 about the axis, prior to the generation of the series of different electrode combinations. In an exemplary embodiment, the controller/processor 80 translates an ideal multipole relative to the electrodes 26 in response to actuation of the initiation control element 118 and the knob 120, such that the different electrode combinations emulate the translation of the ideal multipole.

The programming screen 100 further includes a speed control button 144 with a positive sign (+) and a speed control button 146 with a negative sign (−) to provide the user with visual options to accelerate or decelerate the rate at which the VOA can be displaced relative to the leads 12 or the electrodes 26. Actuating the speed control button 144 increases the speed of steering in comparison to the speed at that instant. Similarly actuating the speed control button 146 decreases the steering speed in comparison to the speed of steering at that instant. Alternatively, the user can release the speed control buttons 144 and 146 to set the speed of steering at a rate at which the speed was being varied, at that instant. Such speed variations generate new stimulation parameters that will proportionately change the rate at which the locus of the VOA will be displaced.

The current steering through directional input controls 120, 124, 126 and the speed variation of the current steering through speed control buttons 144, 146 may be conducted by the user simultaneously.

The programming screen 100 further provides a termination control "stop" button 140, which when actuated instantly terminates the speed variation of the current steering. The button 140 may use different luminance intensity to visually indicate the on/off stage of speed variation. If the speed is being varied, the representation of the control button 140 may have more luminance, and if actuated to turn off speed variation, the button 140 may visually decrease the lower luminance to indicate the speed variation has been ceased.

The programming screen 100 further provides a timing control element 142 to set the duration for which the current steering may be enabled or disabled. The controller/processor 80 is configured for, in response to actuation of the timing control element 142, generating the series of different combinations of the electrodes for a specified time period, such that the translation of the VOA ceases when the time period has elapsed.

Figure 8:
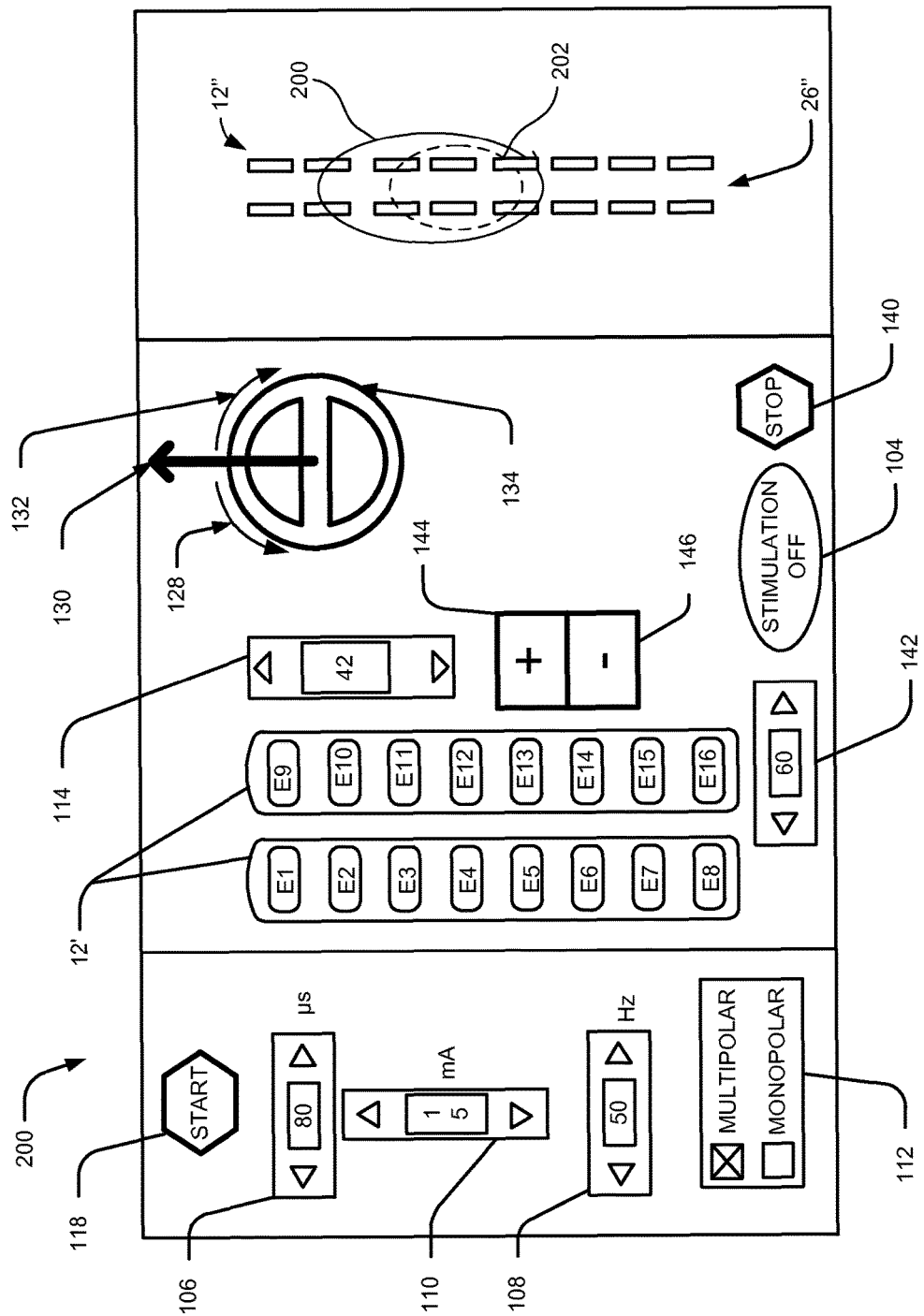
FIG. 8 is the user interface of FIG. 7, in accordance with a second embodiment of the present disclosure.

As one example, and with reference to FIG. 7, an exemplary programming screen 100 (FIG. 8) generated by the CP 18 to allow a user to program the IPG 14 will now be described. The programming screen 200 includes similar elements as provided by the programming screen 100, except that the knob 120 is replaced by a wheel 134 that acts as a current steering direction control element. The wheel 134 further includes a single directional arrow 130 placed at the center of the wheel 134. The arrow 130 may act as the visual pivot for the wheel 134 about which it is rotated and provides visual indication of the direction in which the user intends to steer the locus of VOA with respect to the axis of the leads 12 and electrodes 26. The arrow 130 may have a large width and may employ varying color composition and luminance to visually highlight the direction in which the wheel 134 may be rotated at any instant.

The programming screen 200 further provides a pair of single directional arrows 128, 132, positioned and aligned along the outer circumferential periphery of the wheel 134. Alternatively, the arrows 128, 132 may be positioned inside the wheel 134. The arrows 128 and 132 are curved in opposite directions to each other, to indicate counter-clockwise and clockwise directions respectively. As described above in conjunction with FIG. 7, the arrows 128 and 132, when actuated, emulate the functionality provided by rotating the wheel 134, in small increments. For example, when the arrow 128 is actuated the wheel 134 rotates in the counter-clock direction and when the arrow 132 is actuated, the wheel 134 rotates in the clockwise direction. The arrows 128, 132 can be actuated in a single continuous or multiple discreet times to impart the wheel 134 with the desired degree of rotation. The wheel 134, when rotated, provides the directional input control to displace locus of the electrical stimulation field (and thus, the VOA), relative to the axis of the leads 12 or the electrode 26, in the direction in which the wheel 134 has been rotated.

Although the techniques have been described as being implemented by the CP 18, these techniques may be alternatively or additionally implemented by the RC 16. Furthermore, although particular embodiments of the present inventions have been shown and described, it will be understood that it is not intended to limit the present inventions to the disclosed embodiments, and it will be obvious to those skilled in the art that various changes and modifications may be made without departing from the spirit and scope of the present inventions. Thus, the present embodiments are intended to cover alternatives, modifications, and equivalents, which may be included within the spirit and scope of the invention as defined by the claims.

What is claimed is:

1. An external control device for use with a two-dimensional array of electrodes implanted within tissue and a neurostimulator capable of delivering electrical stimulation energy to the electrodes to create a volume of activation, comprising:
   a user interface including a current steering initiation control element and a current steering direction control element capable of being rotated about an axis;
   a controller/processor configured for, in response to actuation of the initiation control element, generating a series of different combinations of the electrodes in a manner that the volume of activation gradually translates in a specific direction when the electrical stimulation energy is delivered to the different electrode combinations, the controller/processor further configured for, in response to rotation of the direction control element about the axis, defining the specific direction in which the volume of activation is translated; and
   output circuitry configured for transmitting the different electrode combinations to the neurostimulator.

2. The external control device of claim 1, wherein the user interface includes a display screen configured for displaying the direction control element as a graphical element configured for being rotated by a pointing element.

3. The external control device of claim 1, wherein the direction control element takes the form of a knob.

4. The external control device of claim 1, wherein the direction control element takes the form of a wheel.

5. The external control device of claim 1, wherein the direction control element includes an arrow that indicates the specific direction in which the volume of activation is translated.

6. The external control device of claim 1, wherein the direction control element is capable of being selectively rotated about the axis in a clockwise direction and a counterclockwise direction, and the controller/processor is configured for, in response to rotation of the direction control element about the axis in the clockwise direction, adjusting the direction in which the volume of activation is translated in a first direction, and in response to rotation of the direction control element about the axis in the counterclockwise direction, adjusting the direction in which the volume of activation is translated in a second direction opposite to the first direction.

7. The external control device of claim 1, wherein the different electrode combinations are different fractionalized electrode combinations.

8. The external control device of claim 1, wherein the controller/processor is configured for defining the specific direction in response to the actuation of the direction control element prior to the generation of the series of different electrode combinations.

9. The external control device of claim 1, wherein the controller/processor is configured for defining the specific direction in response to the actuation of the direction control element while the series of different electrode combinations are being generated.

10. The external control device of claim 1, wherein the user interface includes a display screen configured for displaying the volume of activation relative to the electrode array, and the controller/processor is configured for estimating the volume of activation based on the different electrode combinations.

11. The external control device of claim 1, wherein the controller/processor is configured for translating an ideal multipole relative to the electrode array in response actuation of the initiation control element, and wherein the different electrode combinations emulate the translation of the ideal multipole.

12. The external control device of claim 1, wherein the user interface further includes a current steering speed control element, and the controller/processor is configured for, in response to actuation of the speed control element, modifying the manner in which the electrode combinations are generated to adjust the speed at which the volume of activation translates.

13. The external control device of claim 12, wherein the speed control element has an acceleration sub-element and a deceleration sub-element, and the controller/processor is configured for, in response to actuation of the acceleration sub-element, modifying the manner in which the electrode combinations are generated to increase the speed at which the volume of activation translates, and in response to actuation of the deceleration sub-element, modifying the manner in which the electrode combinations are generated to decrease the speed at which the volume of activation translates.

14. The external control device of claim 1, wherein the user interface further includes a current steering time control element, and the controller/processor is configured for, in response to actuation of the time control element, generating the series of different combinations of the electrodes for a specified time period, such that the translation of the volume of activation ceases when the time period has elapsed.

15. The external control device of claim 1, wherein the output circuitry comprises telemetry circuitry.

16. The external control device of claim 1, further comprising a housing containing the user interface, controller/processor, and output circuitry.

17. A neurostimulation system, comprising:
   at least one neurostimulation lead configured for being implanted within tissue, the at least one neurostimulation lead carrying a plurality of electrodes capable of being arranged in a two-dimensional pattern;
   a neurostimulator configured for delivering electrical stimulation energy to the electrodes to create a volume of activation; and
   an external control device including a current steering direction control element capable of being rotated about an axis, the external control device configured for prompting the neurostimulator to deliver the electrical stimulation energy to the electrodes in a manner that gradually translates the volume of activation in a specific direction, and for defining the specific direction in which the volume of activation is translated in response to rotation of the direction control element about the axis.

18. The neurostimulation system of claim 17, wherein external control device is further configured for displaying the direction control element as a graphical element configured for being rotated by a pointing element.

19. The neurostimulation system of claim 17, wherein the direction control element takes the form of a knob.

20. The neurostimulation system of claim 17, wherein the direction control element takes the form of a wheel.

21. The neurostimulation system of claim 17, wherein the direction control element includes an arrow that indicates the specific direction in which the volume of activation is translated.

22. The neurostimulation system of claim 17, wherein the direction control element is cap able of being selectively maneuvered about the axis in a clockwise direction and a counterclockwise direction, and the external control device is configured for, in response to rotation of the direction control element about the axis in the clockwise direction, adjusting the direction in which the volume of activation is translated in a first direction; and in response to rotation of the direction control element about the axis in the counterclockwise direction, adjusting the direction in which the volume of activation is translated in a second direction opposite to the first direction.

23. The neurostimulation system of claim 17, wherein the external control device is configured for defining the specific direction in response to the actuation of the direction control element prior to prompting the neurostimulator to deliver electrical stimulation energy to the electrodes in a manner that gradually translates the volume of activation in the specific direction.

24. The neurostimulation system of claim 17, wherein the external control device is configured for defining the specific direction in response to the actuation of the direction control element while the neurostimulator is delivering the electrical stimulation energy to the electrodes in a manner that gradually translates the volume of activation in the specific direction.

25. The neurostimulation system of claim 17, wherein the external control device is configured for adjusting the speed at which the volume of activation translates.

26. The neurostimulation system of claim 17, wherein the external control device is configured for defining a time period and automatically ceasing translation of the volume of activation when the time period has elapsed.

* * * * *